United States Patent [19]

Chapman et al.

[11] 4,075,382

[45] Feb. 21, 1978

[54] DISPOSABLE NONWOVEN SURGICAL TOWEL AND METHOD OF MAKING IT

[75] Inventors: Benjamin E. Chapman, Memphis, Tenn.; Danny R. Moore, Perry, Fla.; Arthur F. Phillips, Memphis, Tenn.

[73] Assignee: The Procter & Gamble Company, Cincinnati, Ohio

[21] Appl. No.: 690,514

[22] Filed: May 27, 1976

[51] Int. Cl.$^2$ ............... B32B 3/02; B32B 7/14; B32B 27/10

[52] U.S. Cl. .................. 428/192; 128/156; 128/296; 156/219; 156/290; 428/198; 428/507; 428/511; 428/515; 428/517

[58] Field of Search ........... 428/192, 193, 194, 198, 428/195, 332, 507, 508, 509, 517, 515, 516, 519, 511; 128/156, 296; 156/88, 219, 220, 290

[56] References Cited

U.S. PATENT DOCUMENTS

| | | | |
|---|---|---|---|
| 3,053,252 | 9/1962 | Wolf | 128/296 |
| 3,434,472 | 3/1969 | Herniman et al. | 128/296 |
| 3,654,060 | 4/1972 | Goldman | 128/156 X |
| 3,881,210 | 5/1975 | Drach et al. | 128/296 X |
| 3,886,942 | 6/1975 | Bernardin | 128/296 X |
| 3,888,248 | 6/1975 | Moore et al. | 128/296 X |
| 3,916,447 | 11/1975 | Thompson | 128/296 X |
| 3,967,623 | 6/1976 | Butterworth et al. | 128/156 X |
| 3,971,381 | 7/1976 | Gibson | 128/296 |

*Primary Examiner*—Thomas J. Herbert, Jr.
*Assistant Examiner*—R. Eugene Varndell, Jr.
*Attorney, Agent, or Firm*—Melville, Strasser, Foster & Hoffman

[57] ABSTRACT

A nonwoven disposable towel, having particular utility as a surgical towel, comprising a five-ply structure and method of making it. The outermost plies of the towel are tissue. To each of these tissue plies there is adhered an intermediate ply constituting a medium density, thermoplastic, long fibered, nonwoven material. These tissue-intermediate ply assemblies comprise primary laminates accounting for four plies of the towel. Between these primary laminates there is located a fifth or center ply constituting a low density, melt blown, long fibered, nonwoven material. The entire structure is heat sealed about its periphery and additional spot heat bonds may be employed to minimize slippage between the center ply and the two primary laminates. The two primary laminates may be embossed prior to assembly of the towel.

26 Claims, 3 Drawing Figures

DISPOSABLE NONWOVEN SURGICAL TOWEL AND METHOD OF MAKING IT

BACKGROUND OF THE INVENTION

1. Field of the Invention

The invention relates to a disposable towel and its method of manufacture, and more particularly to such a towel having particular utility as a surgical towel and comprising a unique five-ply structure including three thermoplastic, long fibered, nonwoven plies and two outermost tissue plies.

2. Description of the Prior Art

While the nonwoven, disposable towels of the present invention may have many uses, they are particularly suited for use as surgical towels and will be described in terms of that application.

In preparation for surgery, the surgeon (as well as the scrub nurse and other members of the operating team) will exercise much care in scrubbing his hands and arms prior to entering the operating theatre. Then, after entering the operating theatre with his hands and arms still wet from the scrub, the surgeon must exercise as much care in the drying of his hands as in the scrubbing operation itself to prevent any contamination of his now clean, but obviously not sterile, hands. While procedures vary from hospital-to-hospital and from doctor-to-doctor, in general a towel is very carefully manipulated by a surgeon after scrubbing so as to dry his hands without introducing any contamination. Usually, one side of the towel is reserved for the drying of each hand and separate portions of the towel are used for each wiping action. This avoids contamination from hand-to-hand. In view of these procedures it is desirable that the towel being used demonstrates a minimum of moisture strike through.

While composite nonwoven surgical towels have been substituted for the more common woven surgical towels, they have not met with universal acceptance. This is true not so much because they fail to perform adequately from the standpoint of absorbency, drying ability and the like, but largely because they lacked the bulk, softness, drape, surface feel and cloth-likeness of the traditional woven surgical towel. Additionally, such composite nonwoven surgical towels generally demonstrated too much strike through. Where steps were taken to prevent such strike through, the remaining characteristics listed above were even more lacking.

The present invention is directed to a nonwoven disposable towel having high absorptive capacity and excellent drying ability with a minimum of strike through. Typically, a surgeon may have from about 15 to about 20 grams of water remaining on his hands and arms after the scrubbing operation. If he is a large man, he may have as much as 30 grams of water remaining. The towel of the present invention has an absorptive capacity of about 4 to about 7 grams of water per gram of towel and weighs about 30 grams. Therefore, the towel of the present invention has a capacity of at least about 4 to 7 times the maximum amount of water to be absorbed from the surgeon's hands and arms.

The towel of the present invention is substantially low in lint tendency, demonstrating excellent abrasion resistance, strength and sturdiness. At the same time, the towel is characterized by markedly improved appearance and surface feel. The towel is soft, cloth-like and is further characterized by desirable bulk, good conformability and drape. Drape, for example, is needed to prevent contamination of the towel. If the towel is too stiff it will have a tendency to rub against the surgeon's scrub suit. This is also true if the towel, to provide sufficient absorptive capacity, must be made too long, too wide or both. Finally, the towel of the present invention may be easily and inexpensively manufactured and readily sterilized.

While particularly adapted for use as surgical towels, the nonwoven, disposable towel structures of the present invention may have many applications. For example, they may be used as professional towels or as hand towels or bath towels for hospital patients and the like. They may serve as disposable towels for use in hotels and motels or for use in institutions such as nursing homes, metal institutions, prisons and the like.

SUMMARY OF THE INVENTION

The nonwoven disposable towel of the present invention is made up of five plies. The outermost or surface plies are tissue plies. Various types of tissue may be used, as will be described hereinafter. Each tissue ply had adhered to its inner or unexposed surface an intermediate ply of a medium density, thermoplastic, long fibered, nonwoven material. The two tissue-intermediate ply assemblies comprise what will be termed hereinafter; "primary laminates". Between the two primary laminates there is located a fifth or center ply of low density, melt-blown, long fibered, nonwoven material. The medium density intermediate plies and the low density center ply are preferably formed of melt-blown polypropylene. Since this material is hydrophobic in nature, the center and intermediate plies of polypropylene are treated with a wetting agent to increase absorbancy.

The primary laminates are preferably subjected to hot or cold embossing and/or mechanical micro-compaction. This improves the surface texture, softness and appearance of the towel structure. When the primary laminates include outer plies of cellulose tissue, they are sprayed or coated on their tissue side with a material commonly used as wet resin to increase the wet abrasion resistance of the end product to withstand the hand and arm drying action of a surgeon, for example. The wet strength resin also ties down any loose cellulosic fibers.

When the primary laminates are located to either side of the center ply, the edges of the towel structure are heat sealed, thereby joining the primary laminates to the center ply. To prevent shifting of the center ply with respect to the primary laminates during a drying and wiping action, additional spot heat bonds may be made throughout the length and width of the towel structure, totally randomly or in a patterned arrangement which may additionally enhance the appearance of the towel.

DESCRIPTION OF THE PREFERRED EMBODIMENTS

Figure 2:
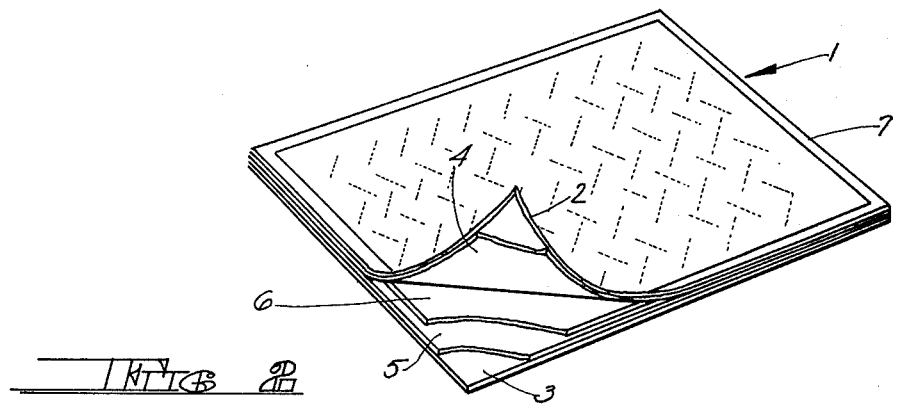
FIG. 2 is a perspective view of the towel of FIG. 1 and illustrating the individual plies thereof, the thickness of the plies being greatly exaggerated for purposes of clarity.

Turning to the Figures wherein like parts have been given like index numerals, the towel of the present invention is generally indicated at 1. As is clear from FIG. 2, the towel is made up of five plies. In FIG. 2 the five plies have been exaggerated in thickness for purposes of clarity.

The outermost plies 2 and 3 are made of tissue. Tissue plies 2 and 3 are followed by intermediate plies 4 and 5 formed from medium density, thermoplastic, long fibered, nonwoven webs. Finally, the fifth or center ply 6, located between intermediate plies 4 an 5, is formed from a low density, melt-blown, long fibered, nonwoven web.

Each of the five plies 2 though 6 must have certain characteristics. The outermost tissue plies 2 and 3 must be characterized by fast strike through, abrasion resistance, low linting tendencies, softness, flexibility, drape and wet strength. In addition, these plies should present a good visual appearance inclusive of surface characteristics, texture and color, if a color is used. Finally, the outermost plies should be characterized by an excellent tactile impression, again inclusive of surface characteristics, texture and the like.

The intermediate plies 4 and 5 should have a medium density. While other nonwoven material may be used, the intermediate plies 4 and 5 are preferably made up of thermoplastic fibers heat sealable to the center ply 6. Plies 4 and 5 must also be capable of adhesive bonding to outermost tissue plies 2 and 3. The intermediate plies should be soft, flexible and possessed of adequate drape. They should also permit fast strike through and be inherently wetable or capable of being rendered wetable.

In addition to the characteristics listed for the tissue and intermediate plies, the primary laminates made therefrom should be embossable. Preferably, they should be heat embossable and heat setable. As a consequence of the characteristics of the tissue and intermediate plies making up each primary laminate, each primary laminate will display an adequate ability to absorb the stretch and energy of a wiping action. They will have good visual appearance and tactile impression. Above and beyond the necessary wet strength, the primary laminates will be low in linting tendencies and high in abrasion resistance. The primary laminates will permit fast strike through of moisture to the center ply.

The center ply serves as the reservoir for the mositure absorbed by the towel structure and should be inherently wettable or capable of being rendered wettable. It therefore should have high absorptive capacity and a wicking rate greater than that of the primary laminates. The center ply should be bulky and of low density, soft, bendable and capable of adequate drape. The combination of absorptive capacity, wicking rate and bulk of the center ply 6 enables the towel structure to demonstrate a minimum of strike through from one outside surface to the other outside surface. While center ply 6 may be made of any appropriate nonwoven material it is preferably made up of melt-blown, nonwoven, long fibered material, heat bondable to the adjacent primary laminates.

Outermost plies 2 and 3 may be made of any appropriate tissue having a basis weight of from 10 to 30 g/m$^2$. The tissue may be made from wet-strength paper, carded webs, air-laid bonded fibrous webs, spun bonded webs, wet laid cellulose webs containing some long cellulose or synthetic fibers, melt-blown polymer webs or the like. While not intended to be so limited, the plies 2 and 3 may be made of a wet strength cellulose tissue of the type taught in U.S. Pat. No. 3,301,746, in the name of Sanford, et al, dated Jan 31, 1967. Preferably a conventional cellulose tissue made on conventional tissue machines is used.

As indicated above, intermediate plies 4 and 5 are preferably made of thermoplastic fibers. They may be produced from spun bonded webs, for example. Preferably, they are derived from a medium density, melt-blown, long fibered, nonwoven web. Such melt-blown webs are taught, for example, in the article entitled SUPERFINE THERMOPLASTIC FIBERS by Van A. Wente appearing in INDUSTRIAL AND ENGINEERING CHEMISTRY, Aug. 1956, Volume 48, No. 8 (pp. 1342–1346). While the melt-blown material may be nylon, polyester, or the like, a melt-blown polypropylene web is preferred.

Where a melt-blown polypropylene web is used for intermediate plies 4 and 5, the composition should be primarily linear polypropylene and the bonding should be medium. The web preferably has a basis weight of from about 10 to about 30 g/m$^2$ and preferably about 15 g/m$^2$. The web filaments should have a diameter of from about 1 to about 8 microns and preferably less than 4 microns. The web should be characterized by a tensile strength of from about 0.5 to about 1.5 lbs./in.; a minimum Elmendorf tear strength of at least about 20 g. in the machine and cross machine directions; a minimum elongation at maximum force of at least about 25% in the machine direction and at least about 35% in the cross direction; and a low load density of from about 0.06 to about 0.09 g/cc.

The low load density is determined in the following manner. The material to be tested is conditioned in a room maintained at 23 ± 1° C (73.4 ± 2° F) and 50 ± 2% relative humidity for a minimum of twelve hours prior to testing. The material to be tested must have an area large enough to provide a sufficient number of thickness measurements to accurately represent the material. Normally, five different locations will be sufficient to determine the average thickness of a nonwoven fabric material. The thickness is measured with a motorized, dead weight micrometer (having a total load of 300 g.) which lowers the micrometer anvil at a uniform rate and pressure on the surface of the material. Five determinations are made on each sample. The median value is reported as the thickness in inches of the material. The low load density of a material is determined by the following calculation:

$$\text{Low Load Density g/cc} = \frac{\text{basis wt. in g/m}^2 \times 0.0000394}{\text{thickness in inches}}$$

The center ply 6 is preferably made from a nonwoven web of any appropriate super fine melt-blown, long fibered material. Again, polypropylene is preferred, the center ply 6 being a low density, lightly bonded ply having a composition comprising primarily linear polypropylene and having a basis weight of from about 20 to about 60 g/m$^2$ and preferably about 30 g/m$^2$. Again, the filament diameter should be from about 1to about 8 microns. The ply 6 should be characterized by a tensile strength less than 1.5 lbs./in. in both the machine and cross machine directions; an Elmendorf tear strength of from about 80 to about 300 g. and preferably 150–300 g.

in both the machine and cross machine directions; a minimum elongation at maximum force of about 35% in the machine direction and about 50% in the cross direction; and a low load density of from about 0.05 to about 0.08 g/cc.

Since polypropylene fibers are inherently hydrophobic, it is necessary that the nonwoven melt-blown polypropylene plies 4, 5 and 6 be treated with a wetting agent, as will be described hereinafter.

The melt-blown polypropylene ply 4 is attached to tissue ply 2 by an appropriate adhesive, as will be described hereinafter. Similarly, the melt-blown polypropylene ply 5 is affixed to tissue ply 3.

It has been found that by providing intermediate plies 4 and 5 affixed to tissue plies 2 and 3 (respectively) and a loose center ply 6 free of adhesive or binder, the resultant towel has a softness, resiliency, bulk, cloth-likeness and absorptive capacity far superior to prior art structures, as, for example, a structure wherein tissue plies are adheared directly to a single, central melt-blown polypropylene web.

Figure 1:
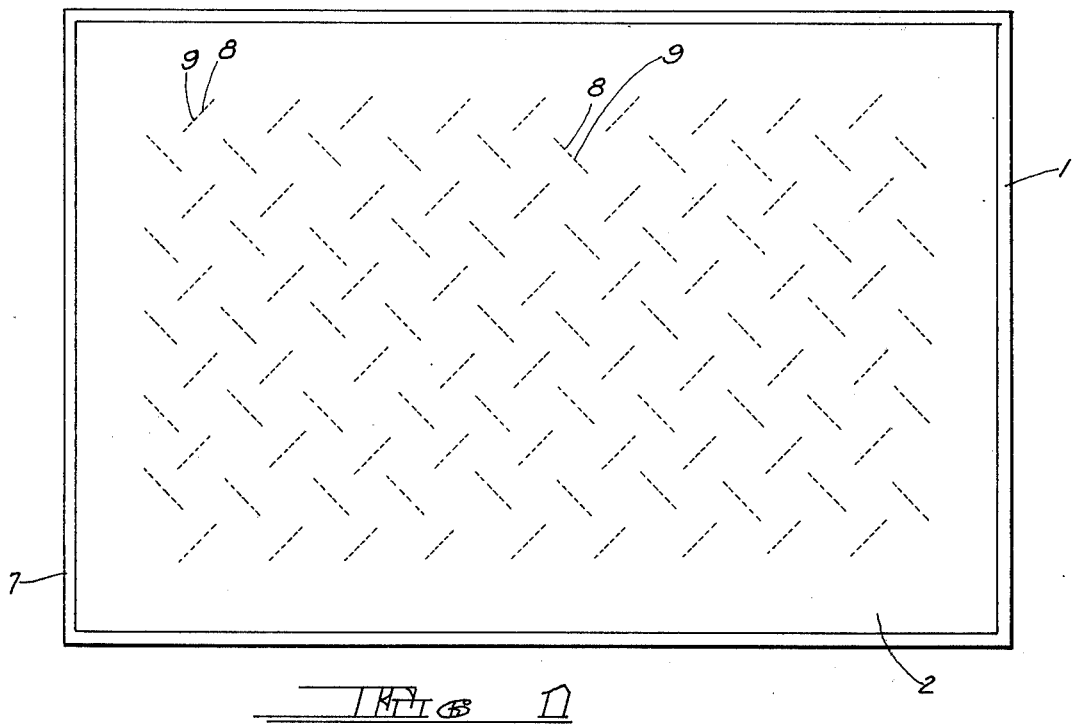
FIG. 1 is a plan view of the towel of the present invention.

The structure thus far described is bonded about its periphery, as at 7 in FIGS. 1 and 2. This prevents loose fiber migration from plies 4, 5 and 6 and joins center ply 6 to the primary laminates 2-4 and 3-5. While the structure may be adhesively bonded about its periphery, it is preferably heat sealed.

Where the towel of the present invention is to be used primarily as a wiping device (as in its use as a hand and arm drying surgical towel), it is preferable to further join the center ply 6 and primary laminates 2-4 and 3-5 so as to prevent them from slipping or shifting with respect to each other during the application of shear force resulting from a wiping action. Such ply slippage may be prevented by providing a plurality of discrete spot bonds of the center ply 6 and primary laminates 2-4 and 3-5. While adhesive spot bonding may be used, spot heat bonding is preferred. For purposes of an exemplary showing, the towel of FIG. 1 is illustrated as having a plurality of individual spot heat bonds 8 arranged in rows 9. The rows 9, in turn, are arranged in a decorative "chevron" pattern. At the position of each individual spot heat bond, the towel structure is stiffened and its absorptive capacity is reduced. Nevertheless, when appropriately designed and positioned, the spot heat bonds will cause no appreciable effect on the softness, resiliency and drape of the overall towel structure and no significant effect on its absorptive capacity.

The length, width, size and shape of the individual spot heat bonds 8 may be varied, as may be the overall pattern thereof. The spot heat bonds may, for example, be so positioned as to "channel" movement of moisture in the towel. In addition to their functional purpose, the spot heat bonds 8 may also serve as decorative elements of the towel. Where the tissue layers 2 and 3 are colored, the individual spot heat bonds will have a darker shade. The effect provides a towel having a 2-tone coloring system of enhanced appearance.

It has also been found preferable to hot or cold emboss the primary laminates 2-4 and 3-5. For example, the primary laminates may be passed through the nip of a heated embosser having one steel engraved roll and one soft back-up roll, as is known in the art. As a result of the embossing treatment, the primary laminates are partially densified and rendered resistant to mild wet or dry expansive forces. The primary laminates are improved in tactile impression, softness, flexibility and surface character, the overall stiffness of the primary laminates being reduced.

Figure 3:
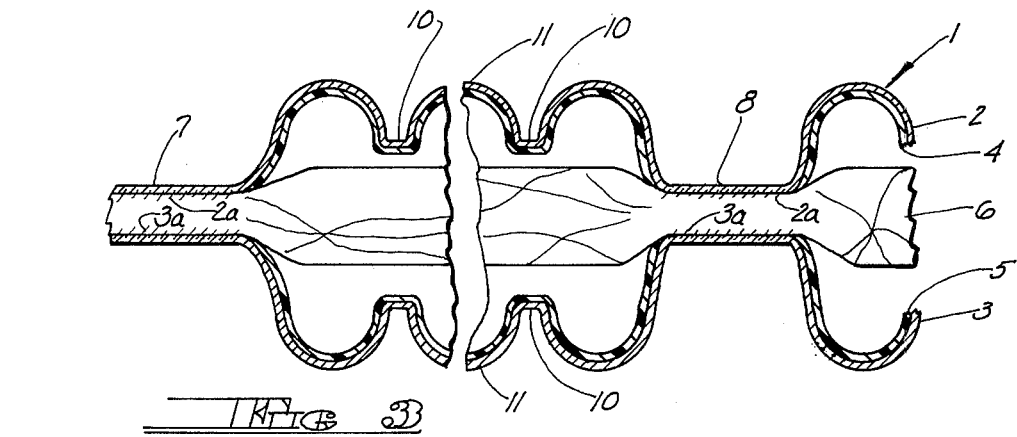
FIG. 3 is a fragmentary view diagramatically illustrating the cross section of the towel structure.

FIG. 3 diagramatically illustrates an idealized showing of the towel of the present invention with the primary laminates 2-4 and 3-5 having been hot embossed. The primary laminates will have, as a result of the hot embossing, areas 10 of high density and areas 11 of low density. The heat used in the embossing step is such that the areas 10 are heat set but maintain their fibrous structure. This heat setting results in a structure which retains its embossing under conditions of further processing, sterilization, high humidity and during use of the towel. As is to be expected, the absorptive capacity of the hot embossed primary laminates, as compared to unembossed primary laminates, is decreased. Unexpectedly, however, it has been found that the absorptive capacity of the total towel structure 1 is substantially increased when the primary laminates 2-4 and 3-5 have been hot embossed as compared to a total towel structure with unembossed primary laminates. The embossing of the primary laminates also improves the appearance and tactile impression of the towel. Another way to improve the appearance and tactile impression is to subject the primary laminates 2-4 and 3-5 to mechanical micro-compaction (as for example taught in U.S. Pat. No. 2,624,245, in the name of S. L. Cluett, and dated Jan. 6, 1953) in lieu of or in addition to an embossing treatment.

FIG. 3 also illustrates a sealed edge 7 of the towel structure and a spot heat bond 8. In these areas the plies 4, 5 and 6 melt together and partially, at least, impregnate the tissue plies 2 and 3 as indicated by hatch lines 2a and 3a.

The exterior surfaces of the towel (i.e., the tissue surfaces) are preferably treated with a wet strength resin when a cellulose tissue is used. This increases wet abrasion resistance. and tends to tie down loose cellulosic fibers on the towel surfaces. An application of latex could also be used for these purposes, but care must be exercised to assure that such a latex application does not decrease the desired fast strike through of the primary laminates or deleteriously effect the tactile impression.

In the manufacture of the towel of the present invention, the primary laminates 2-4 and 3-5 are assembled. Since the primary laminates are identical, it is only necessary to describe the assembly of one. The tissue web or ply and the thermoplastic intermediate web or ply are joined together by an appropriate binder. The binder should be soft, flexible, safe for use in the operating room and wettable. The binder is applied as a high viscosity solution to the thermoplastic, nonwoven intermediate web by any appropriate means such as a padder, a gravure roll applicator, a metering applicator or the like, minimum penetration of the thermoplastic, nonwoven intermediate web by binder being desired. If the intermediate web is melt-blown, the non-wire side has more loose fibers and is preferably, from a bond strength stand point, the side laminated to the tissue. The tissue and the thermoplastic nonwoven plies are brought together under light pressure (of the order of about 60 pounds per linear inch) between laminating rolls. The primary laminate is thereafter dried and cured on conventional steam heated dryer drums, a yankee dryer or the like. A hot air dryer or other conventional means may be used. The curing and drying step should be conducted at a temperature such that the intermediate plies maintain their fibrous structure. The dried and cured primary laminate may be used directly in the further towel making process or rolled for subsequent use.

Appropriate acylic latex binders are, for example, manufactured by Rohm & Haas Company, of Philadelphia, Pennsylvania, under the designation E-751 (a soft, hydrophillic acrylic polymer designed as a binder) or by B. F. Goodrich, Chemical Company, of Cleveland, Ohio, under the trademark Hycar and designation 2600×223 (a soft, hydrophillic, acrylic polymer designed as a binder). To control penetration of the latex into the thermoplastic nonwoven intermediate web and the tissue web, the viscosity and the percent binder solids should be high. The above mentioned binders are furnished with a solids content of about 46% and about 50%, respectively. Percentages as low as about 35% have been used successfully. To raise the viscosity of the binder to the desired level to control its penetration and thus improve bond strength by confining the latex near the interface of the tissue and intermediate plies, athickener suitable for use with the latex binder should be added. Sufficient thickener should be added to obtain at least about a 7000 cps or greater viscosity. Viscosities as high as 40,000 to 60,000 have produced primary laminates of acceptable bond strength. Exemplary thickeners are manufactured, for example, by Rohm & Haas Company, of Philadelphia, Pennsylvania under the trademark ACRYSOL and the designations ASE 60 or ASE 75 (alkali-soluble emulsions comprising acylic polymers containing acidic functional groups). To the thickened latex binder ammonium hydroxide may be added to obtain a binder solution having a pH of 7 or greater. Finally, an antifoam agent may be added to improve the processability of the binder solution. Excellent results have been achieved, for example, through the use of a silicone antifoam agent added in the range of from 2 to 4 grams per pound of binder solution. An exemplary silicon antifoam agent is manufactured by General Electric, of Waterford, New York, under the designation AF-72 (an aqueous emulsion of a dimethyl polysiloxane containing about 30% silicone solids).

As mentioned above, most thermoplastic polymers used in nonwonvens are generally hydrophobic and must be treated with a wetting agent if they are to be hydrophillic as is required for plies 2, 3, 4, 5 and 6. The term wetting agent as used herein is intended to encompass any chemical additive or treatment step rendering the thermoplastic nonwoven webs hydrophillic. In the case of a chemical additive it may be applied in a number of different ways. First of all, the polymer may be treated as a part of the manufacturing process of the nonwoven webs. For example, a wetting agent may be added at the time the filaments of the web are formed. Another approach is to treat the already formed polymer filamets or nonwoven webs. Thus, that web from which center ply 6 is made may be dipped in a wetting agent bath and caused to pass between squeeze rolls, or the wetting agent may be applied by spraying. Thereafter, the treated web is dried over conventional steam heated drying drums or by other conventional drying methods.

The thermoplastic webs from which plies 4 and 5 are formed (and plies 2 and 3 if hydrophobic in nature) can be treated in precisely the same manner before of after lamination to the tissue layer. Treatment of a thermoplastic web after its lamination to the tissue web is convenient because the laminate may be dipped in a wetting agent bath, caused to pass through squeeze rolls, sprayed with a wet-strength resin (if required) and dried over conventional steam heated dryer drums. Thus the wetting agent and wet-strength resin treatments can be accomplished in a single line.

As heretofore pointed out, one preferable thermoplastic nonwoven web suitable for plies 4, 5 and 6 is a melt-blown polypropylene web of filaments of average diameter of from about 1 to about 8 microns and referably less than 4 microns. With such a melt-blown polypropylene web, excellent results have been achieved through the use of a 0.4% to a 1.2% application by weight of a wetting agent manufactured by Textilana Corporation of Hawthorne, California, under the tradename Velvetex BCW (a biodegradable, chemically stable, liquid coco fatty betaine). Excellent results have also been achieved through the use of a 4% application by weight of a wetting agent manufactured by Emery Industries of Cincinnati, Ohio, under the designation 9886A (a liquid partial ester of polyglycerol). The above noted wetting agents not only increase the absorbency of the melt-blown polypropylene webs and make them softer, but they also lower the surface resistivity of the webs to an acceptable level (i.e., as described in NFPA standard 56A) for use in an operating room or the like.

An appropriate resin, such as a resin used as a wet strength resin in papermaking, may be used to increase the wet abrasion resistance of the tissue plies, particularly in the case of cellulose tissues or tissues containing some cellulose fibers. Excellent results have been achieved, for example, through the use of a wet strength resin manufactured by Hercules Incorporated of Wilmington, Delaware under the trademark Kymene and designated 557H, as a 0.6% to 1.2% surface addition, based on laminate weight, applied to the tissue side of the primary laminates. Kymene 557H is a resin sold as a wet strength additive for paper making and is a cationic water soluble polyamine-polyamide epichlorohydrin.

After treatment with the wetting agent and the wet strength resin, the primary laminates may be cold or hot embossed (by methods well known in the art) and/or subjected to mechanical micro-compaction of the type taught in the above mentioned U.S. Pat. No. 2,624,245.

Final assembly of the towels of the present invention is accomplished by passing a web constituting center ply 6 and webs constituting primary laminate 2–4 and primary laminate 3–5 between deeply relieved and heated sealing rolls for simultaneously forming the edge seals 7 and spot heat bonds 8, while not contacting the remainder of the towel structure. These rolls will seal individual towel segments which may thereafter be cut into separate towels. The same rolls may be used to provide a line of perforations between adjacent towels of the web so that the towels may be maintained in web form, but readily removed from the web, one at a time.

The towel structures of the present invention may be sterilized by any appropriate method, either by the manufacturer or the user.

EXAMPLE

In the practice of the present invention a conventional wet strength cellulose tissue, having a basis weight of about 15 g/m$^2$, is bonded to a medium density melt-blown polypropylene web having a basis weight of about 15 g/m$^2$ with an appropriate latex binder (as described above) and dried and cured over conventional steam heated dryer drums. The primary laminate thus formed is dipped in a wetting agent bath, caused to pass through squeeze rolls, sprayed with a wet strength resin on its tissue side and thereafter dried over conventional steam heated dryer drums, again as described above. The primary laminate is then hot embossed.

The resulting primary laminate is characterized by a basis weight of 38 gm/m², excellent absorbency and strike through, a Klemm vertical wicking rate of 26/16 in./min., good drape and conformability, a lint release upon vigerous agitation in an air flow for 30 minutes of 10 mg/yd² and a wet tensile strength (MD/CD) of 1.55/.90 lb./in.

Primary laminates of the type just described are located to either side of a center ply with the tissue side of the primary laminates outermost. The primary laminates and center ply are caused to pass between deeply relieved and heated sealing rolls to from edge seals and spot heat bonds therebetween.

The center ply is preferably a low density ply of super fine, melt-blown long fibered polypropylene. The center ply is characterized by a basis weight of 30 g/m², a Klemm vertical wicking rate of 28/16 in./min. and an absorptive capacity (1 psi loading) of 6 g H₂O/g web.

The resulting finished products are in the form of towels 16 by 24 in. having an absorptive capacity (1 psi loading) of 5.0 g H₂O/g towel, a lint level of 20 mg/yd² and an Elmendorf tear strength of 200 g.

Towels thus made have all of the desired characteristics for use as a surgical towel discussed above, including absorptive capacity, bulk, softness, drape, tactile impression, low lint releast and the like.

Modifications may be made in the invention without departing from the spirit of it.

The embodiments of the invention in which an exclusive property or privilege is claimed are defined as follows:

1. A disposable, sterilizable, surgical towel having a five-ply construction comprising a center ply of wettable microfibrous melt-blown fibers having a basis weight of from about 20 to about 60 grams per square meter and two identical primary laminates to each side of said center ply and each comprising an intermediate ply of wettable thermoplastic fibers having a basis weight of from about 10 to about 30 grams per square meter adhesively secured to a tissue ply having a basis weight of from about 10 to about 30 grams per square meter, said tissue plies comprising the outermost plies of said towel, said center ply and said primary laminates being bonded together about the periphery of said towel.

2. The structure claimed in claim 1 wherein said intermediate plies each have a basis weight of about 15 grams per square meter.

3. The structure claimed in claim 1 wherein said center ply has a basis weight of about 30 grams per square meter.

4. The structure claimed in claim 1 wherein said primary laminates are cold embossed.

5. The structure claimed in claim 1 wherein said primary laminates are hot embossed.

6. The structure claimed in claim 1 wherein said tissue plies are wet strength resin treated plies.

7. The structure claimed in claim 1 wherein said fibers of said intermediate and center plies are wetting agent treated melt-blown polypropylene fibers.

8. The structure claimed in claim 1 wherein said center ply has an absorptive capacity and a wicking rate such as to minimize strike through from one outermost ply to the other outermost ply of said towel.

9. The structure claimed in claim 1 wherein each of said tissue plies is a wet strength paper tissue.

10. The structure claimed in claim 2 wherein said tissue plies have a basis weight of 15 g/m².

11. The structure claimed in claim 1 wherein said center ply and said primary laminates ar additionally joined by a plurality of individual spot bonds so arranged as to minimize shifting of said center ply and said primary laminates when said towel is used with a wiping action and without significant effect on the softness and absorptive capacity of the towel.

12. The structure claimed in claim 11 wherein said tissue plies are wet strength resin treated plies and said primary laminates are hot embossed.

13. The structure claimed in claim 11 wherein said bond about the periphery of the towel and said spot bonds are heat bonds.

14. A disposable towel having a five-ply construction comprising a low density, soft, bulky, bendable, wettable, highly absorbent, nonwoven center ply and two identical primary laminates to each side of said center ply, each of said primary laminates comprising an inner ply and an outer ply adhesively adheared together, said inner ply comprising a medium density, soft, bendable, wettable, nonwoven ply, said outer ply comprising an abrasion resistant, low linting, soft, bendable, tissue ply, said primary laminates being characterized by fast strike through, said tissue plies comprising the outermost plies of said towel, said center ply and said primary laminates being bonded together about the periphery of said towel.

15. The structure claimed in claim 14 wherein said center ply has a basis weight of from about 20 to about 60 grams per square meter and said intermediate and said tissue plies have a basis weight of from about 10 to about 30 grams per square meter.

16. The structure claimed in claim 14 wherein said primary laminates are cold embossed.

17. The structure in claim 14 wherein said primary laminates are hot embossed.

18. The structure claimed in claim 14 wherein said tissue plies are wet strength resin treated plies.

19. The structure claimed in claim 14 wherein said fibers of said intermediate and center plies are wetting agent treated melt-blown polypropylene fibers.

20. The sturcture claimed in claim 14 wherein said center ply has an absorptive capacity and a wicking rate such as to minimize strike through from one outermost ply to the other outermost ply of said towel.

21. The structure claimed in claim 14 wherein each of said tissue plies is a wet strength paper tissue.

22. The structure claimed in claim 21 wherein said tissue plies have a basis weight of 15 g/m².

23. The structure claimed in claim 14 wherein said intermediate plies have a basis weight of about 15 grams per square meter and said center ply has a basis weight of about 30 grams per square meter.

24. The structure claimed in claim 23 wherein said tissue plies are wet strength resin treated plies and said primary laminates are hot embossed.

25. The structure claimed in claim 14 wherein said center ply and said primary laminates are additionally joined by a plurality of individual spot bonds so arranged as to minimize shifting of said center ply and said primary laminates when said towel is used with a wiping action and without significant effect on the softness and absorptive capacity of the towel.

26. The structure claimed in claim 25 wherein at least one of said center ply and said inner plies is thermoplastic and wherein said bond about the periphery of the towel and said spot bonds are heat bonds.

* * * * *